United States Patent
Hogendijk et al.

(10) Patent No.: US 7,666,216 B2
(45) Date of Patent: Feb. 23, 2010

(54) DELIVERY CATHETER FOR RIBBON-TYPE PROSTHESIS AND METHODS OF USE

(75) Inventors: Michael Hogendijk, Palo Alto, CA (US); Todd Thompson, San Jose, CA (US); Miles Alexander, Fremont, CA (US)

(73) Assignee: Novostent Corporation, Mountain View, CA (US)

( * ) Notice: Subject to any disclaimer, the term of this patent is extended or adjusted under 35 U.S.C. 154(b) by 579 days.

(21) Appl. No.: 10/772,764

(22) Filed: Feb. 4, 2004

(65) Prior Publication Data

US 2004/0158308 A1    Aug. 12, 2004

Related U.S. Application Data

(63) Continuation-in-part of application No. 10/342,427, filed on Jan. 13, 2003.

(60) Provisional application No. 60/436,516, filed on Dec. 24, 2002.

(51) Int. Cl.
*A61F 2/06* (2006.01)
*A61F 11/00* (2006.01)

(52) U.S. Cl. .................................. 623/1.11; 606/108

(58) Field of Classification Search ............... 623/1.11, 623/1.12; 606/108, 191, 194, 195, 198
See application file for complete search history.

(56) References Cited

U.S. PATENT DOCUMENTS

| 4,768,507 | A | 9/1988 | Fischell et al. |
| 6,238,430 | B1 | 5/2001 | Klumb et al. |
| 6,248,122 | B1 | 6/2001 | Klumb et al. |
| 6,273,910 | B1 * | 8/2001 | Limon ..................... 623/1.15 |
| 6,508,834 | B1 | 1/2003 | Pinchasik |
| 6,533,805 | B1 | 3/2003 | Jervis |
| 6,572,643 | B1 | 6/2003 | Gharibadeh |
| 6,576,006 | B2 | 6/2003 | Limon et al. |
| 6,699,275 | B1 * | 3/2004 | Knudson et al. ........... 623/1.12 |
| 7,008,446 | B1 * | 3/2006 | Amis et al. ................ 623/1.21 |
| 7,303,758 | B2 * | 12/2007 | Falotico et al. ............. 424/424 |

OTHER PUBLICATIONS

Office Action mailed Mar. 25. 2008; U.S. Appl. No. 10/836,909, filed Apr. 30, 2004.

* cited by examiner

*Primary Examiner*—Vy Q Bui
(74) *Attorney, Agent, or Firm*—James F. Hann; Haynes Beffel & Wolfeld LLP

(57) ABSTRACT

The present invention is directed to a delivery catheter for use in deploying a vascular prosthesis having a self-expanding radial distal section joined to a helical section for use in a wide range of interventional applications. The delivery catheter comprises an elongated member having a balloon disposed adjacent to a distal end of the member, means for engaging the distal section of the vascular prosthesis against axial translation, and a sheath that restrains the vascular prosthesis against the elongated member during transluminal delivery. The balloon also may be used to perform angioplasty of a stenosis located within the vessel prior to deployment of the vascular prosthesis. Methods of using the delivery catheter of the present invention also are provided.

13 Claims, 5 Drawing Sheets

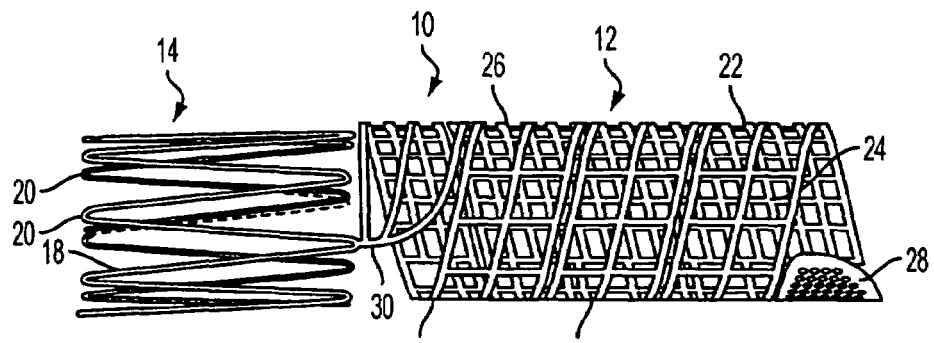
FIG. 1A
FIG. 1B
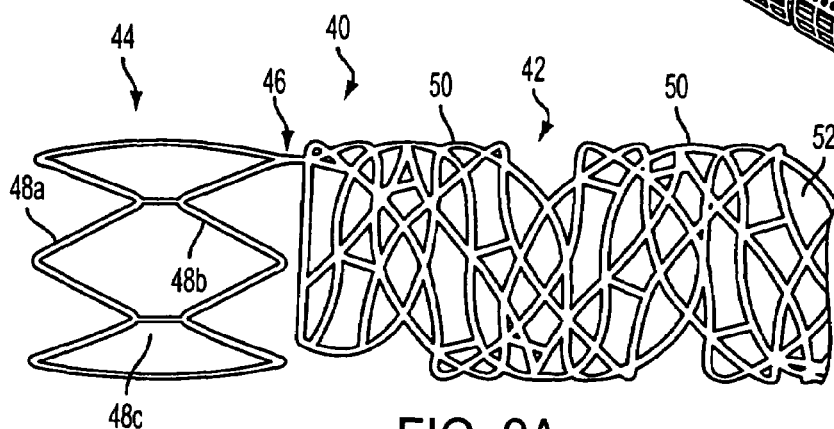
FIG. 2A
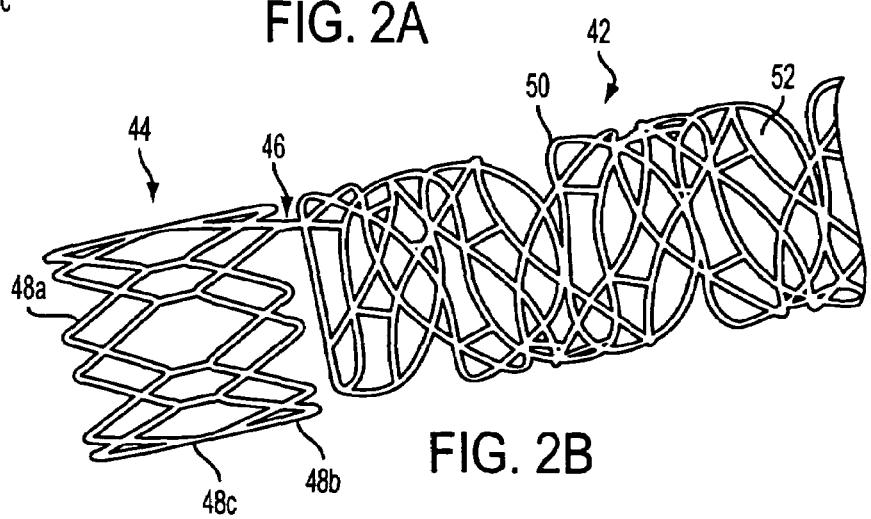
FIG. 2B

DELIVERY CATHETER FOR RIBBON-TYPE PROSTHESIS AND METHODS OF USE

REFERENCE TO RELATED APPLICATIONS

This application is a continuation-in-part of U.S. patent application Ser. No. 10/342,427, filed Jan. 13, 2003, which claims priority from U.S. provisional patent application Ser. No. 60/436,516, filed Dec. 24, 2002.

FIELD OF THE INVENTION

The present invention relates to a delivery catheter, and methods of use, for an implantable vascular ribbon-type prosthesis having a helical section and at least one anchor section, wherein the delivery system reduces stent axial movement during deployment, both with respect to the vessel and the delivery catheter.

BACKGROUND OF THE INVENTION

Today there are a wide range of intravascular prostheses on the market for use in the treatment of aneurysms, stenoses, and other vascular irregularities. Balloon expandable and self-expanding stents are well known for restoring patency in a stenosed vessel, e.g., after an angioplasty procedure, and the use of coils and stents are known techniques for treating aneurysms.

Previously-known self-expanding stents generally are retained in a contracted delivery configuration using a sheath, then self-expand when the sheath is retracted. Such stents commonly have several drawbacks, for example, the stents may experience large length changes during expansion (referred to as "foreshortening") and may shift within the vessel prior to engaging the vessel wall, resulting in improper placement. Additionally, many self-expanding stents have relatively large delivery profiles because the configuration of their struts limits further compression of the stent. Accordingly, such stents may not be suitable for use in smaller vessels, such as cerebral vessels and coronary arteries.

Other drawbacks associated with the use of coils or stents in the treatment of aneurysms is that the devices, when deployed, may have a tendency to straighten or otherwise remodel a delicate cerebral vessel, which may cause further adverse consequences. Moreover, such devices may not adequately reduce blood flow from the cerebral vessel into the sac of the aneurysm, which may increase the likelihood of rupture. Generally, if a greater surface area is employed to cover the sac, the delivery profile of the device may be compromised due to the increased surface area, and the device also may be more rigid and cause remodeling of the vessel.

For example, PCT Publication WO 00/62711 to Rivelli describes a stent comprising a helical mesh coil having a plurality of turns and including a lattice having a multiplicity of pores. The lattice is tapered along its length. In operation, the plurality of turns are wound into a reduced diameter helical shape, then constrained within a delivery sheath. The delivery sheath is retracted to expose the distal portion of the stent and anchor the distal end of the stent. As the delivery sheath is further retracted, subsequent individual turns of the stent unwind to conform to the diameter of the vessel wall.

The stent described in the foregoing publication has several drawbacks. For example, due to friction between the turns and the sheath, the individual turns of the stent may bunch up, or overlap with one another, when the delivery sheath is retracted. U.S. Pat. Nos. 4,768,507 to Fischell et al. and 6,576,006 to Limon et al., each describe the use of a groove disposed on an outer surface of an interior portion of the stent delivery catheter, wherein at least a portion of the stent is disposed within the groove to prevent axial movement during proximal retraction of the sheath. However, the approach described in those patents results in a larger profile for the delivery catheter than might otherwise be possible.

In addition, once the sheath of the delivery catheter is fully retracted, the turns of a ribbon-type stent may shift within the vessel prior to engaging the vessel wall, resulting in improper placement of the stent. Still further, because the distal portion of the stent may provide insufficient engagement with the vessel wall during subsequent retraction of the remainder of the sheath, ambiguity concerning accuracy of the stent placement may arise.

In addition, when using a ribbon-type stent to restore patency to a vessel following angioplasty, it typically is necessary to first insert a dilatation catheter over a pre-placed guide wire, perform angioplasty, remove the balloon dilatation catheter, and then insert the stent delivery catheter. To minimize the procedure time and trauma associated with exchanging the stent delivery catheter for the balloon dilatation catheter, it would be advantageous to provide a stent delivery catheter for ribbon-type stents that in addition included a balloon component for performing angioplasty prior to delivering the stent.

In view of these drawbacks of previously known devices, it has been proposed in copending and commonly assigned U.S. patent application Ser. No. 10/342,427, filed Jan. 13, 2003, to provide an implantable vascular prosthesis comprising a ribbon-type stent body joined at its distal end to a radially expandable anchor. As described in that application, the radially expandable anchor is deployed first to anchor the distalmost portion of the ribbon-type stent body, thereby enhancing accuracy of placement of the prosthesis.

Although the prosthesis described in the above-mentioned application overcomes many of the drawbacks of previously know ribbon-type stents, it has been observed that some proximal movement of the radially expandable anchor may occur during proximal withdrawal of a sheath used to retain the anchor in its delivery configuration.

It further would be desirable to provide means for anchoring a distal end of the delivery catheter to the vessel wall, prior to deployment of the radially expandable anchor, so as to prevent inadvertent axial movement of the delivery catheter during withdrawal of the sheath of the delivery catheter.

It also would be desirable to provide a delivery catheter suitable for use with ribbon-type stents that permits angioplasty to be performed with the same catheter as used for stent delivery, thereby reducing complexity of the procedure and eliminating a need to exchange a stent delivery catheter for an angioplasty catheter.

SUMMARY OF THE INVENTION

In view of the foregoing, it is an object of the present invention to provide a delivery catheter for use with a ribbon-type stent having a distal radially expandable anchor, wherein the delivery catheter includes a sheath and means for preventing proximal movement of the radially expandable anchor during withdrawal of the sheath that do not enlarge the delivery profile of the delivery catheter.

It is another object of this invention to provide means for anchoring a distal end of a delivery catheter to the vessel wall, prior to deployment of a radially expandable anchor portion of the stent, so as to prevent inadvertent axial movement of the delivery catheter during deployment of the stent.

It is a further object of the present invention to provide a delivery catheter suitable for use with ribbon-type stents that permits angioplasty to be performed with the same catheter as used for stent delivery, thereby reducing complexity of the procedure and eliminating a need to exchange a delivery catheter for an angioplasty catheter.

These and other objects of the present invention are accomplished by providing a delivery catheter for use with a vascular prosthesis comprising a ribbon-type stent body joined at its distal end to a radially expandable anchor, wherein the prosthesis is configured to engage a vessel wall and adapt to a natural curvature of the vessel wall. The delivery catheter of the present invention preferably is configured to accept vascular prostheses having a self-expanding helical ribbon portion and a self-expanding anchor portion comprising either a generally zig-zag or cell-like configuration, wherein the anchor portion is deployed first to fix the distal-most extremity of the stent within a vessel.

In a preferred embodiment, the delivery catheter comprises an inner member slidably received within a sheath, wherein the inner member includes means, disposed adjacent to the distal end of the inner member, for engaging a distal portion of the stent. The means for engaging are configured to prevent axial translation of the anchor portion of the stent during proximal withdrawal of the sheath. Preferably, the means for engaging comprise either a polymer portion that has been treated to enhance its grip on the stent, or features extending from the inner member, such as bumps or protuberances, that interengage the zig-zag or cell-like structure of the radially expandable anchor.

Further in accordance with the preferred embodiment, the delivery catheter includes an inflatable balloon adjacent to the distal end of the inner member, and distal to the distal end of the sheath. When so configured, the inflatable balloon may be deployed to engage a portion of a vessel so that proximal withdrawal of the sheath does not inadvertently result in axial displacement of the delivery catheter or stent relative to the vessel. Advantageously, because the balloon of the delivery catheter of the present invention distributes the load created by proximal withdrawal of the sheath to the entire circumference of the vessel, it reduces local stress concentrations, during deployment of the helical portion of the stent, that would otherwise arise where the radially expandable anchor contacts the vessel wall.

In a particularly preferred embodiment, the means for engaging comprises a proximal shoulder of the balloon, which has been treated to enhance its frictional grip on the distal portion of the stent.

In accordance with yet another aspect of the present invention, the balloon of the delivery catheter may be configured to perform angioplasty of a stenosis within the vessel prior to being deployed to anchor the catheter during stent deployment. In this case, a single catheter may be used both to disrupt the stenosis and deliver the stent, without the additional complexity required to exchange a delivery catheter for an angioplasty catheter.

Methods of using the delivery catheter of the present invention, for example, in the treatment of a stenosis, also are provided.

BRIEF DESCRIPTION OF THE DRAWINGS

Further features of the invention, its nature and various advantages will be more apparent from the accompanying drawings and the following detailed description of the preferred embodiments, in which:

FIGS. 1A-1B are, respectively, side and perspective views of a vascular prosthesis suitable for use with the delivery catheter of the present invention;

FIGS. 2A-2B are, respectively, side and perspective views of an alternative embodiment of vascular prosthesis suitable for use with the delivery catheter of the present invention;

DETAILED DESCRIPTION OF THE INVENTION

Figure 3:
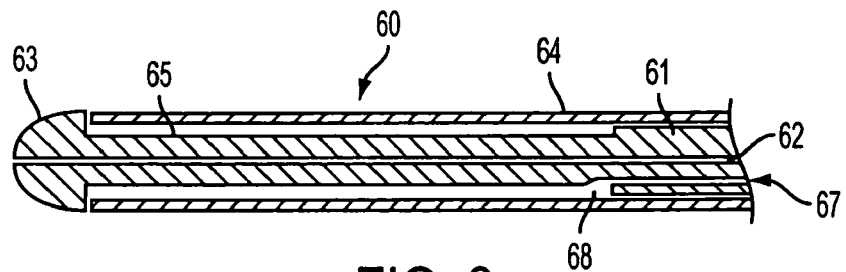
FIG. 3 is a side sectional view of a prior art delivery system that may be used in conjunction with the vascular prosthesis of FIGS. 1 and 2.

The present invention is directed to a delivery catheter for use with an implantable vascular prosthesis configured for use in a wide range of applications, such as treating aneurysms, maintaining patency in a vessel, and allowing for the controlled delivery of therapeutic agents to a vessel wall. The delivery catheter of the present invention is designed for use in delivering a vascular prosthesis having a helical ribbon portion joined, at its distal end, to a radially self-expanding anchor portion. The delivery catheter provides enhanced accuracy in delivering the stent by reducing the risk of bunching of the stent and inadvertent axial movement of the delivery catheter during stent deployment. In addition, the delivery catheter may optionally include an angioplasty balloon to perform angioplasty, thus reducing the number of equipment exchanges required to perform an interventional procedure.

Referring to FIGS. 1A and 1B, a first embodiment of a vascular prosthesis suitable for use with the delivery catheter of the present invention is described. Vascular prosthesis 10 is described in copending commonly assigned U.S. patent application Ser. No. 10/342,427, filed Jan. 13, 2003, and comprises helical section 12 and distal section 14, each capable of assuming contracted and deployed states. In FIGS. 1A and 1B, helical section 12 and distal section 14 are each depicted in their respective deployed states.

Vascular prosthesis 10 preferably is formed from a solid tubular member comprising a shape memory material, such as nickel-titanium alloy (commonly known in the art as Nitinol). The solid tubular member then is laser cut, using techniques that are per se known in the art, to a desired deployed configuration, as depicted in FIG. 1. An appropriate heat treatment, per se known in the art, then may be applied to solid regions 16 of vascular prosthesis 10 while the device is held in the desired deployed configuration (e.g., on a mandrel). The treatment of the shape memory material allows vascular prosthesis 10 to self-deploy to the desired deployed configuration, depicted in FIG. 1, for purposes described hereinafter.

Distal section 14 preferably has a generally zig-zag configuration in the deployed state, wherein the zig-zag configuration preferably is formed by laser cutting a solid tube to form a pattern comprising plurality of struts 18 disposed between plurality of bends 20. Distal section 14 is designed to be deployed from a stent delivery catheter first to fix the distal end of the stent at a desired known location within a vessel, whereby subsequent deployment of helical section 12 of the stent may be accomplished with greater accuracy.

Helical section 12 preferably comprises a helical mesh configuration that includes a plurality of substantially flat turns 22. Plurality of turns 22 may include a multiplicity of openings provided in different shapes and sizes, as illustrated by larger rectangular openings 24, smaller rectangular openings 26 and small circular openings 28. The multiplicity of openings are disposed between solid regions 16 of the shape memory material used to form vascular prosthesis 10, although, the configuration of helical section 12 depicted herein is merely for illustrative purposes. Helical section 12 is coupled to distal section 14 at junction 30.

Referring to FIGS. 2A and 2B, an alternative embodiment of a vascular prosthesis suitable for use with the delivery catheter of the present invention is described. Vascular prosthesis 40 includes helical section 42 and distal section 44 joined at junction 46. Distal section 44 comprises a radially self-expanding cell-like configuration comprising pair zig-zags 48a, 48b joined by struts 48c. The cell configuration of FIG. 2 is expected to be more rigid than the single zig-zag configuration of the embodiment of FIG. 1, and hence capable of applying, and withstanding, greater radial force. Helical section 42 preferably comprises a helical ribbon including plurality of turns 50 having multiplicity of openings 52 provided in varying shapes and sizes.

With respect to FIG. 3, delivery catheter 60 suitable for use in deploying the vascular prostheses of FIGS. 1 and 2 is described. Delivery catheter 60 is similar to that disclosed in U.S. Pat. No. 4,665,918 to Garza et al., and includes inner member 61 having central lumen 62, nose cone 63 and sheath 64. Catheter 61 includes recessed portion 65 that cooperates with sheath 64 to retain the helical section and the distal section of vascular prosthesis, such as that illustrated in FIGS. 1 and 2, in their respective contracted states for translumenal delivery. Delivery catheter 60 also may comprise fluid delivery lumen 67, which may be used to deliver chilled saline to the vascular prosthesis during delivery of the device via one or more ports 68.

Figure 4A:
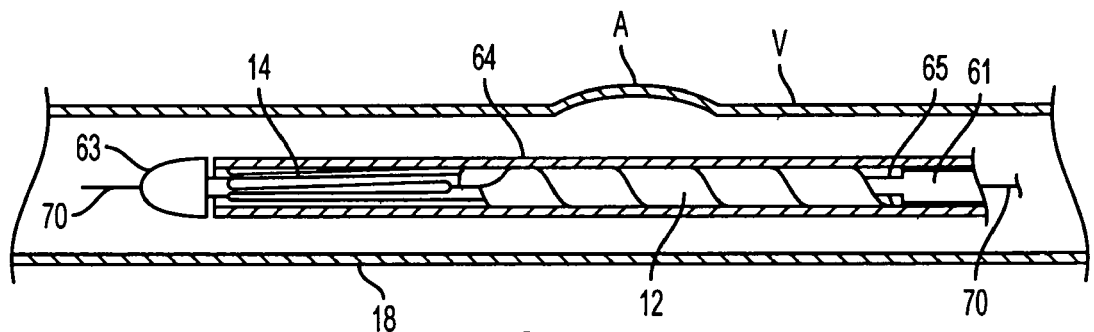
FIGS. 4A-4C are side sectional views illustrating use of delivery catheter of FIG. 3 to deploy a vascular prosthesis of the type shown in FIGS. 1 and 2 to treat aneurysm.
Figure 4B:
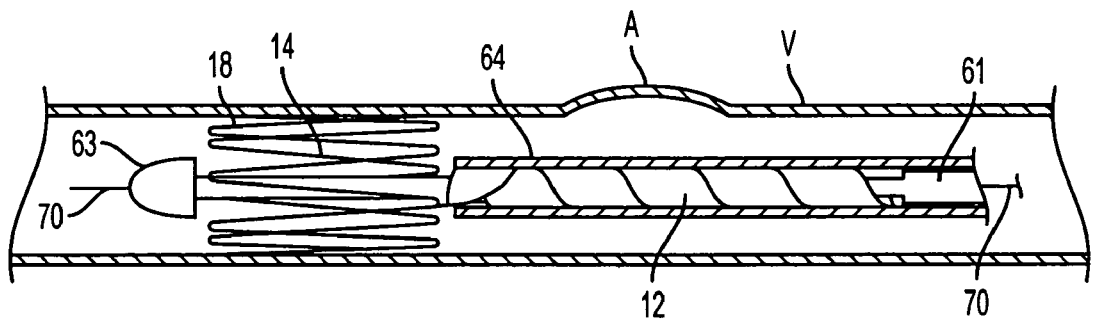
Figure 4C:
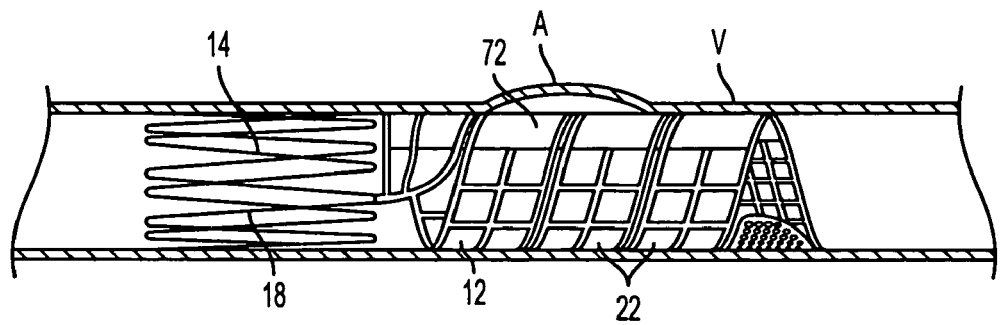

Turning now to FIGS. 4A-4C, a method of delivering a vascular prosthesis, for example, in the treatment of an aneurysm, is described. In FIG. 4A, vascular prosthesis 10 of FIG. 1 is provided in the fully contracted state disposed between recessed portion 65 of inner member 61 and sheath 64 of the delivery catheter of FIG. 3. Specifically, distal section 14 is compressed to its contracted delivery state about recessed portion 65 of catheter 61, and the plurality of turns of helical section 12 are wound down to a contracted delivery state about recessed portion 65, as shown in FIG. 4A. Sheath 64 is disposed over helical section 12 and distal section 14, as depicted, to retain both sections in their contracted states.

To deliver the stent, guide wire 70 is percutaneously and translumenally advanced through a patient's vasculature, using techniques that are per se known in the art, until a distal end of guide wire 70 is positioned distal of aneurysm A, which is situated in vessel V. Delivery system 60, having vascular prosthesis 10 contracted therein, then is advanced over guide wire 70 via central lumen 62 of catheter 61. Nose cone 63 serves as an atraumatic bumper during advancement of delivery system 60. Delivery system 60 is advanced under fluoroscopic guidance until helical section 12 is situated adjacent aneurysm A, as shown in FIG. 4A.

During advancement of delivery system 60 though a patient's vasculature, a chilled fluid, preferably saline, may be delivered to vascular prosthesis 10 via fluid delivery lumen 67 and port 68. The chilled fluid may be used to increase or maintain the flexibility of prosthesis 10 to facilitate advancement of delivery system 60 over guide wire 70.

In a next step, sheath 64 is retracted proximally to cause distal section 14 to self-deploy distal of aneurysm A, as shown in FIG. 4B, so that struts 18 of distal section 14 expand radially to engage an inner wall of vessel V. Because self-expanding distal section generally is expected to be in contact with the interior surface of sheath 64, it is possible that distal section may translate axially (or "bunch-up") on top of the distal edge of helical section 12 during proximal withdrawal of sheath 64. As described hereinbelow, in accordance with one aspect of the present invention, a delivery catheter is provided having means for engaging the distal section to the inner member 61 of the delivery catheter, so as to avert this potential problem.

With distal section 14 anchored distal of aneurysm A, sheath 64 may then be further retracted proximally to cause a distal-most turn of helical section 12 to unwind and deploy to its predetermined shape. As the sheath is further retracted proximally, each subsequent turn of helical section 12 unwinds, one at a time, and engages and conforms to an inner wall of vessel V in a controlled manner. As illustrated in FIG. 4C, stent 10 may include a fluid impermeable covering 72 disposed on a portion of the exterior surface of helical section 12 to isolate aneurysm A from the vessel. When stent 10 is fully deployed, the delivery catheter then is proximally retracted over guide wire 70 and withdrawn from the patient's vessel, and guide wire 70 is removed.

Deploying distal section 14 prior to deploying helical section 12 allows distal section 14 to fix the distal end of the stent to the vessel wall and provides controlled deployment of the helical turns of helical section 12. Applicant has come to appreciate, however, that after deployment of distal section 14, further proximal retraction of sheath 64 to deploy helical section 12 may result in the application of considerable loads to the vessel wall via the distal section. More particularly, under some situations it may be possible that such loads, if concentrated at the points of contact between distal section 14 and the vessel, could cause the distal section undesirably to abrade the vessel wall. Accordingly, it is another aspect of the present invention to provide a delivery system that distributes any loads arising from proximal retraction of the sheath uniformly to the vessel wall.

In addition to the foregoing potential issues, it is possible that movement of the sheath of the delivery catheter may result inadvertently cause the delivery catheter to translate proximally within the vessel prior to deployment of the distal section of the prosthesis, thereby leading to reduced accuracy of the stent placement. In accordance with yet another aspect of the present invention, the delivery catheter of the present invention is configured to reduce the possibility of inadvertent axial translation of the delivery catheter during an initial phase of stent deployment, i.e., prior to deployment of distal section 14.

Figure 5:
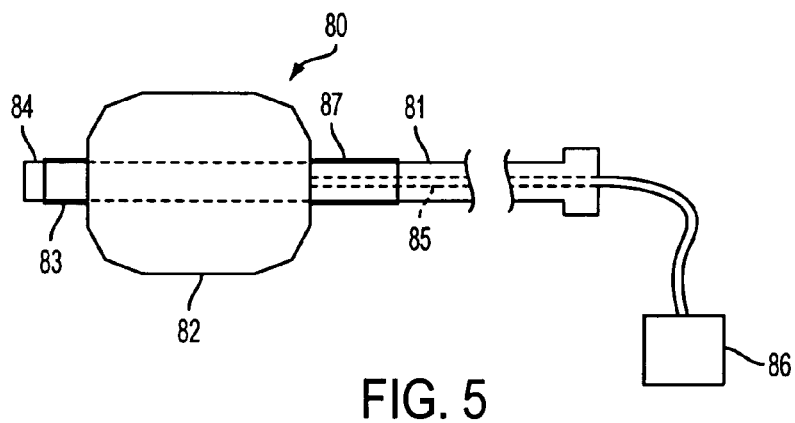
FIG. 5 is a side view of an inner member of a delivery catheter of the present invention.

Referring now to FIG. 5, a first embodiment of an inner member constructed in accordance with the principles of the present invention, and suitable for use in the delivery catheter of FIG. 3, is described. Inner member 80 comprises shaft 81 comprising a sturdy flexible material such as are typically used in catheter manufacture, e.g., polyethylene, and includes balloon 82 disposed adjacent to distal end 83. Radio-opaque marker 84 is affixed to the distal end of shaft 81 to make the distal end of the shaft visible under fluoroscopic imaging.

Balloon 82 may be formed from compliant or semi-compliant materials, such as nylon or PEBAX, and is inflated through lumen 85. Lumen 85 may be pressurized with fluid from syringe or inflator 86, which may be selectively coupled to the proximal end of shaft 81, as is known in the art.

In accordance with the principles of the present invention, inner member 81 includes means for engaging the distal end of the distal section of vascular prosthesis 10, 40, such as illustrated in FIGS. 1 and 2. In one preferred embodiment, the means for engaging comprises polymer layer 87 that has been treated, e.g., by formulation, mechanical abrasion, chemically or by heat treatment, to make the polymer tacky or otherwise enhance the grip of the material. Preferably polymer layer 87 comprises a proximal shoulder of balloon 82, although the polymer layer alternatively may be formed and applied separately from balloon 82. Alternatively, balloon 82 may be omitted, and polymer layer 87 may be disposed on a portion of the catheter adjacent the distal end of the catheter.

Figure 6:
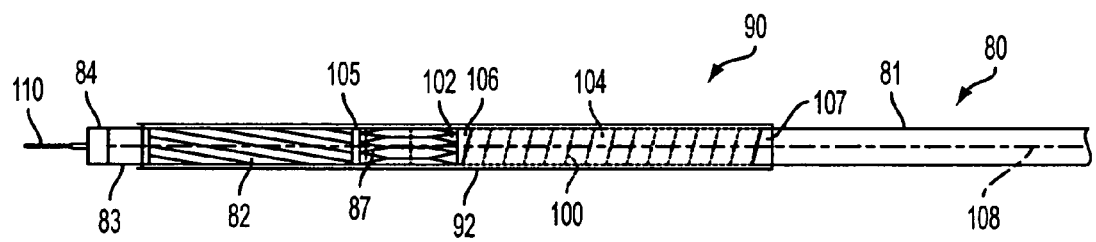
FIG. 6 is a side view, partly in section, illustrating a vascular prosthesis disposed with a delivery catheter constructed in accordance with the present invention.

With respect to FIG. 6, delivery catheter 90 of the present invention is described, wherein vascular prosthesis 100 of the type shown in FIG. 1 is constrained between inner member 80 and sheath. Prosthesis 100 includes distal section 102 that is engaged with polymer layer 87, and helical section 104 that is wrapped to a small diameter around shaft 81 of inner member 80. Sheath 92 restrains vascular prosthesis 100 against shaft 81 of inner member 80 until the sheath is retracted proximally. Balloon 82 is shown deflated and wrapped around shaft 81 of the inner member, in accordance with known techniques.

Sheath 92 is depicted in its insertion configuration, wherein the sheath extends over balloon 82 to a position just proximal of distal end 83. Delivery catheter 90 optionally may include radio-opaque marker bands 105, 106 and 107 disposed, respectively, on inner member 80 beneath the distal and proximal ends of distal section 102 and at the proximal end of helical section 104. Delivery catheter 90 preferably includes guide wire lumen 108 that enables the delivery catheter to be slidably translated along guide wire 110.

In operation, delivery catheter 90 is advanced along a guide wire into a vessel containing a treatment area. Positioning of the vascular prosthesis relative to the treatment area is confirmed using radio-opaque markers 84 and 105-107. Once the delivery catheter is placed in the desired location, sheath 92 is retracted proximally to permit vascular prosthesis 100 to deploy. In accordance with the principles of the present invention, polymer layer 87 grips distal section 102 of stent 100, thereby preventing distal section 102 from being dragged proximally into engagement with helical section 104 during retraction of sheath 92. Instead, polymer section 87 grips distal section 102 against axial movement, and permits the distal section to expand radially outward into engagement with the vessel wall once the sheath is retracted.

In addition, as described with respect to FIG. 8 hereinbelow, either before or after distal section 102 is expanded into engagement with the vessel wall, balloon 82 is expanded to contact the vessel wall. Balloon 82 therefore anchors distal end 83 of delivery catheter 90 relative to the vessel wall, so that no inadvertent axial displacement of the delivery catheter arises during proximal retraction of the sheath to release distal section 102 or helical section 104 of the vascular prosthesis 100.

By comparison, if balloon 82 were not provided on delivery catheter, as depicted in FIG. 4B, the forces applied to retract sheath 92 to release helical section 104 would communicate tensile loads to the vessel wall via distal section 102. This in turn might create high localized loads on the vessel wall where the proximal bends of distal section 102 engage the vessel wall, potentially abrading or injuring the endothelium. By providing balloon 82 however, forces applied to the distal section by proximally retracting the sheath are uniformly distributed to the vessel wall around the circumference of the balloon, thereby avoiding potentially injurious stress concentrations.

Figure 7:
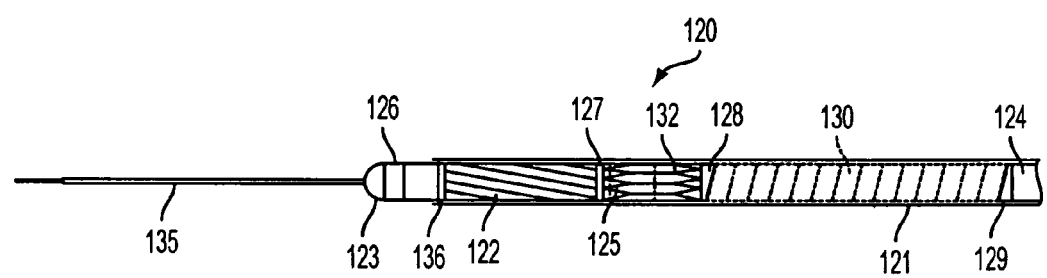
FIG. 7 is a side view, partly in section, illustrating a vascular prosthesis disposed with an alternative delivery catheter constructed in accordance with the present invention.

In FIG. 7, an alternative embodiment of a delivery catheter of the present invention is depicted. Delivery catheter 120 includes vascular prosthesis 130 of the kind depicted in FIG. 1, and differs from delivery catheter 90 of FIG. 6 in that delivery catheter 120 includes atraumatic tip 123 and dilatation balloon 122. Balloon 122 is configured to perform an angioplasty procedure, as well as to anchor the delivery catheter during proximal retraction of sheath 121. Similar to the embodiment of FIG. 6, inner catheter 124 includes polymer layer 125 disposed under distal section 132 of vascular prosthesis to prevent axial movement of the prosthesis during retraction of sheath 121. Delivery catheter 120 also includes optional radio-opaque markers 126-129 and a central lumen that permits the delivery catheter to be advanced over guide wire 135. Delivery catheter 120 also may include radio-opaque marker 136 disposed adjacent to the distal end of the sheath, which may be used to monitor retraction of the sheath under fluoroscopic imaging.

Figure 8:
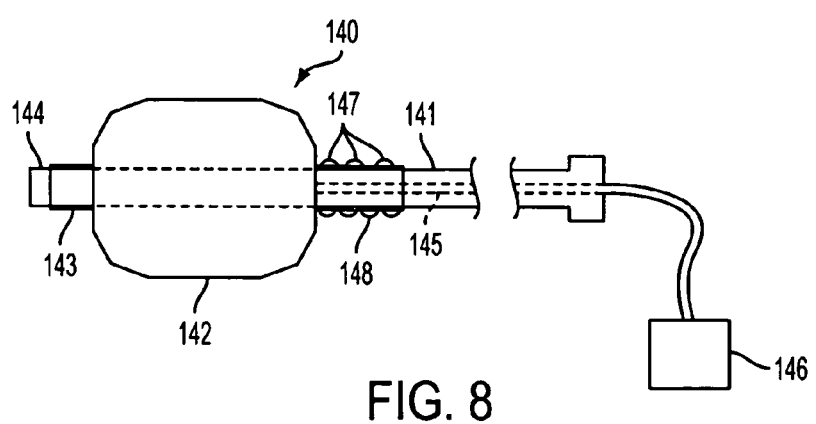
FIG. 8 is a side view of an alternative embodiment of an inner member suitable for use in the delivery catheter of the present invention.

Referring to FIG. 8, an alternative embodiment of an inner member constructed in accordance with the principles of the present invention is described. Inner member 140 comprises shaft 141 comprising a sturdy flexible material such as are typically used in catheter manufacture, e.g., polyethylene, and includes balloon 142 disposed adjacent to distal end 143. Radio-opaque marker 144 is affixed to the distal end of shaft 141 to make the distal end of the shaft visible under fluoroscopic imaging. Balloon 142 may be formed from compliant or semi-compliant materials, such as nylon or PEBAX, and is inflated through lumen 145. Lumen 145 may be pressurized with fluid from syringe or inflator 146, which may be selectively coupled to the proximal end of shaft 141, as for the embodiment of FIG. 5.

Inner member 141 includes means for engaging the distal end of the distal section of vascular prosthesis 10 or 40 of FIGS. 1 and 2, wherein the means for engaging comprises raised features 147 that interengage the struts of the distal section of the vascular prosthesis to grip of the distal section. Preferably, features 147 comprise bumps or protuberances formed on proximal shoulder 148 of balloon 142, although the features alternatively may be formed and applied to inner member 141 separately from balloon 142. Features 147 also may comprise ribs, ridges, grooves, notches and selectively inflatable sections. As for the embodiment of FIG. 5, inner member preferably includes a guide wire lumen extending along its length.

With further reference to FIG. 9, methods of using delivery catheter 120 of the present invention are described to perform angioplasty and deliver a vascular prosthesis of the type shown in FIGS. 1 and 2. Vascular prosthesis 150 is disposed in its delivery configuration compressed around inner member 124 and retained by sheath 121. Distal section 152 of the stent 150 is disposed in contact with polymer layer 125 to prevent relative axial movement therebetween.

Figure 9A:
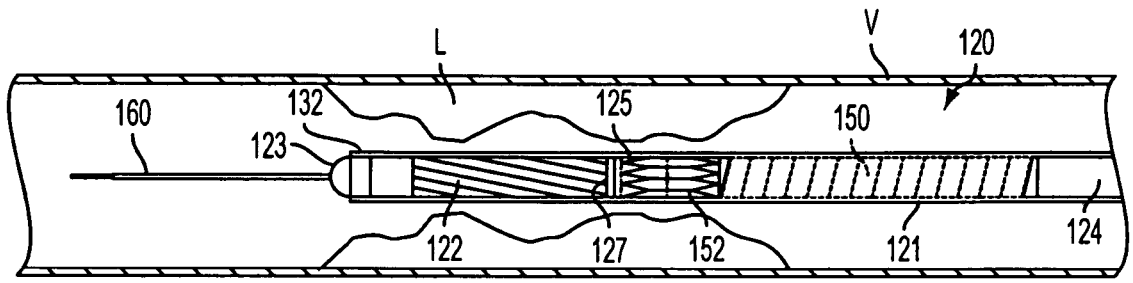
FIGS. 9A to 9G are side-sectional views showing a method of performing angioplasty and delivering a vascular prosthesis using the delivery catheter of the present invention.
Figure 9B:
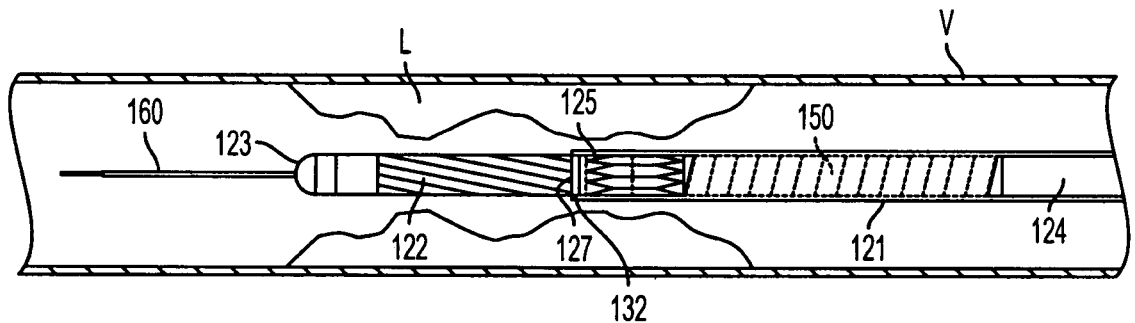

As shown in FIG. 9A, delivery catheter 120 is percutaneously and transluminally advanced along guide wire 160 until tip 123 of the catheter is disposed within lesion L within body vessel V, for example, as determined by fluoroscopic imaging. Once balloon 122 is positioned adjacent lesion L, sheath 121 is retracted proximally until radio-opaque marker 132 on sheath 121 is aligned with marker 127 of inner member 124, thereby indicating that the sheath has been retracted clear of balloon 122, as shown in FIG. 9B.

Figure 9C:
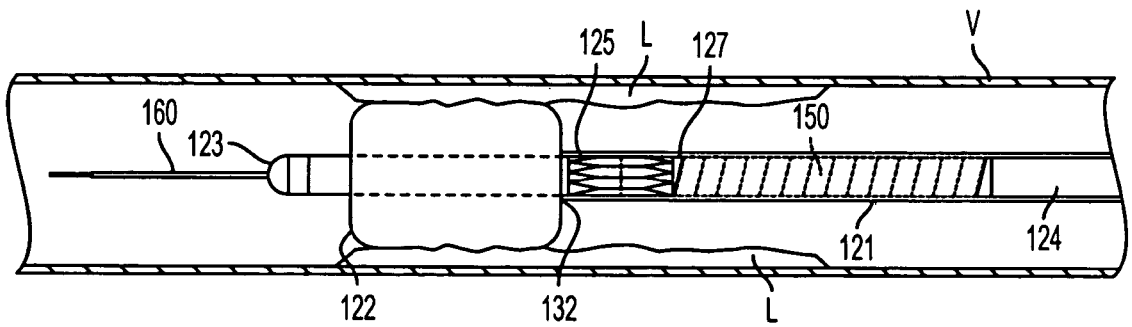

With respect to FIG. 9C, once balloon 122 is positioned adjacent lesion L, the balloon may be inflated to dilate a portion of the vessel and disrupt the plaque comprising lesion L. Balloon 122 then may be deflated, moved to another location within the lesion, and re-inflated to disrupt another portion of lesion L. This process is repeated until the lesion has been sufficiently disrupted to restore patency to the vessel.

Figure 9D:
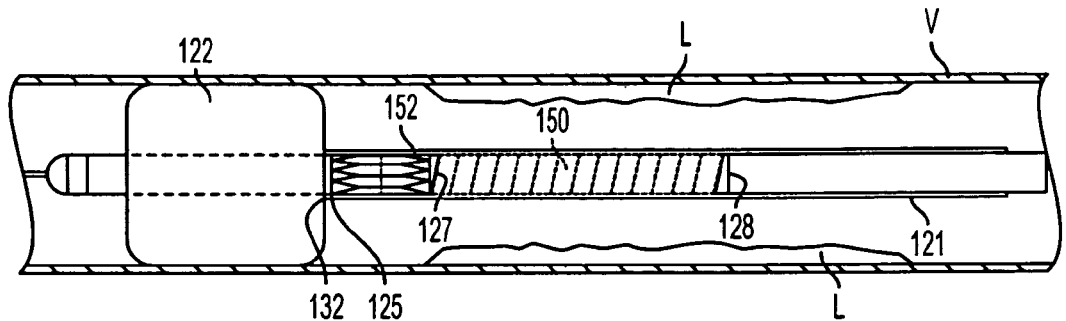

Referring to FIG. 9D, after performing angioplasty, delivery catheter 120 is advanced so that balloon 122 is disposed adjacent healthy tissue, distal of the lesion. Balloon 122 then is inflated to engage the vessel wall and prevent axial displacement of the delivery catheter during subsequent retraction of sheath 121. Polymer layer 125 engages distal section 152 of vascular prosthesis 150, thereby preventing axial displacement of distal section 152 during retraction of sheath 121.

Figure 9E:
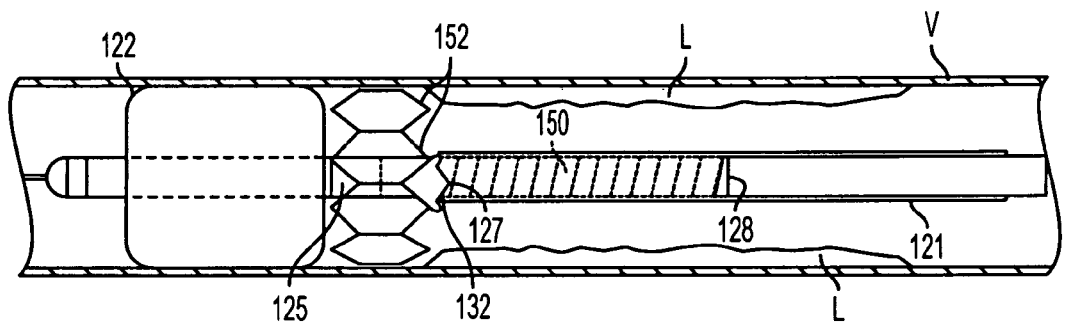

Referring to FIG. 9E, after balloon 122 is inflated to engage the vessel wall, sheath 121 is retracted proximally until distal section 152 self-expands into engagement with vessel wall within or distal to lesion L. Proximal movement of sheath 121 may be halted once radio-opaque marker 132 of sheath 121 is substantially aligned with radio-opaque marker 127 of inner member 124. When released from the constraint provided by sheath 121, the struts of distal section 152 expand in a radial direction to engage the interior of vessel V.

Figure 9F:
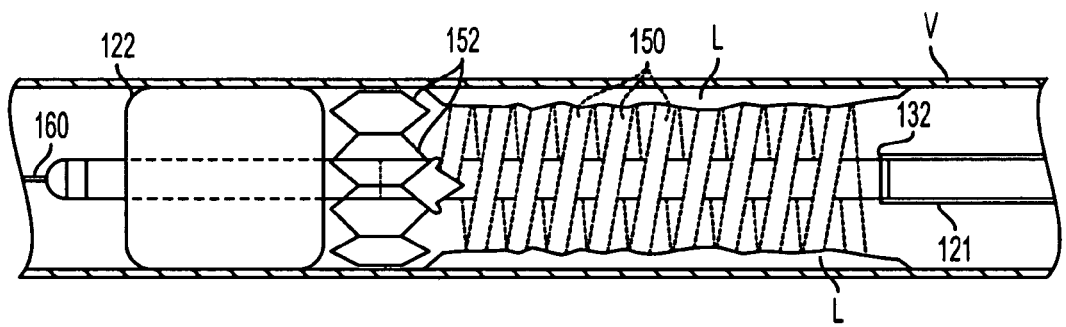
Figure 9G:
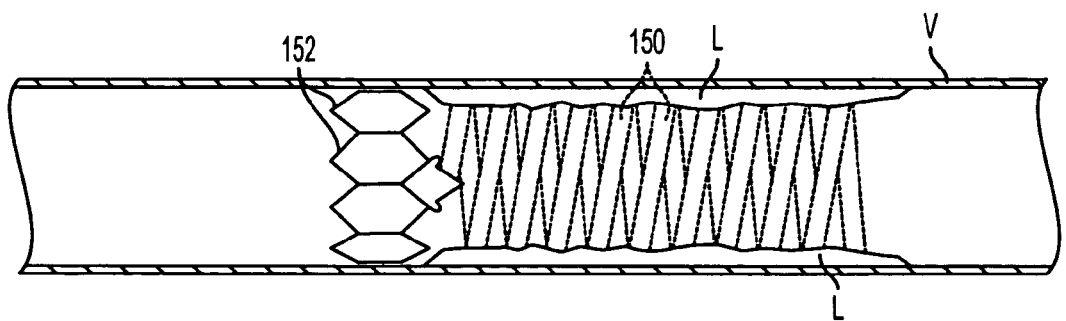

Referring now to FIG. 9F, after distal section 152 is secured to the vessel wall distal of lesion L, sheath 121 is further retracted proximally to cause the helical section of stent 150 to unwind and deploy to its predetermined shape within vessel V. During proximal retraction of sheath 121, each subsequent turn unwinds one at a time and engages and conforms to an inner wall of vessel V in a controlled manner. Advantageously, any forces that might be applied to distal section 152 during retraction of sheath 121 are uniformly distributed over the surface of balloon 122, thereby reducing the risk of insult to the vessel endothelium. Once the last turn of the helical section of stent 150 is deployed, balloon 122 is deflated, the sheath optionally may be advanced to cover balloon 122. Delivery catheter 120 then is withdrawn from the patient's vessel, and guide wire 160 is removed.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A catheter for delivering a vascular prosthesis within a body vessel, the vascular prosthesis having a distal section and a proximal section, the catheter comprising:
   an inner member comprising:
      an elongated member having distal and proximal ends; and
      a radially expandable balloon attached to the elongated member adjacent to the distal end, the balloon having a radially expandable length;
   a sheath slideably disposed over at least a portion of the inner member to restrain the vascular prosthesis against the elongated member during translational insertion of the catheter;
   the radially expandable balloon comprising a non-radially expandable proximal shoulder;
   the non-radially expandable proximal shoulder comprising means for engaging the distal section of the vascular prosthesis to prevent axial translation of the vascular prosthesis during proximal retraction of the sheath;
   the means for engaging comprising means for enhancing frictional engagement with the distal section of the vascular prosthesis; and
   the means for engaging comprising proximal of the whole radially expandable length of the balloon.

2. The catheter of claim 1, wherein the means for enhancing frictional engagement comprises a polymer layer that has been treated to enhance frictional engagement with the distal section of the vascular prosthesis.

3. The catheter of claim 1, wherein the means for enhancing frictional engagement comprises raised features that inter-engage the distal section of the vascular prosthesis.

4. The catheter of claim 3, wherein the raised features are chosen from the group consisting of ribs, bumps, ridges, grooves, notches and selectively inflatable sections.

5. The catheter of claim 1, wherein the balloon is configured to engage a wall of the body vessel during deployment of the distal section of the vascular prosthesis to prevent axial displacement of the catheter relative to the body vessel.

6. The catheter of claim 1, wherein the balloon is configured to perform angioplasty of a stenosis disposed within the body vessel.

7. The catheter of claim 1, further comprising at least one radio-opaque marker disposed on the elongated member and a radio-opaque marker disposed adjacent to a distal end of the sheath.

8. The catheter of claim 1, wherein the elongated member further comprises an atraumatic tip disposed on the distal end and a lumen extending between the distal and proximal ends, the lumen dimensioned to slideably receive a guide wire.

9. A catheter for delivering a vascular prosthesis within a body vessel, the vascular prosthesis having a distal section and a proximal section, the catheter comprising:
   an inner member comprising:
      an elongated member having distal and proximal ends; and
      a balloon attached to the elongated member adjacent to the distal end;
      the radially expandable balloon comprising a non radially expendable proximal shoulder;
   a sheath slideably disposed over at least a portion of the inner member to restrain the vascular prosthesis against the elongated member during transluminal insertion of the catheter;
   a non-radially expandable polymer layer affixed directly to the elongated member at the non-radially expandable proximal shoulder of the balloon, the polymer layer comprising means for engaging the distal section of the vascular prosthesis and enhancing the grip of the polymer layer to the vascular prosthesis to help prevent axial translation of the vascular prosthesis during proximal retraction of the sheath.

10. The catheter of claim 9, wherein the polymer layer defines raised features that inter-engage the distal section of the vascular prosthesis.

11. The catheter of claim 9, wherein the balloon is configured to engage a wall of the body vessel during deployment of the distal section of the vascular prosthesis to prevent axial displacement of the catheter relative to the body vessel.

12. The catheter of claim 9, wherein the balloon is configured to perform angioplasty of a stenosis disposed within the body vessel.

13. The catheter of claim 9, further comprising at least one radio-opaque marker disposed on the elongated member and a radio-opaque marker disposed adjacent to a distal end of the sheath.

* * * * *

UNITED STATES PATENT AND TRADEMARK OFFICE
CERTIFICATE OF CORRECTION

| | |
|---|---|
| PATENT NO. | : 7,666,216 B2 |
| APPLICATION NO. | : 10/772764 |
| DATED | : February 23, 2010 |
| INVENTOR(S) | : Hogendijk et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 998 days.

Signed and Sealed this

Seventh Day of December, 2010

David J. Kappos
*Director of the United States Patent and Trademark Office*